US006190404B1

(12) United States Patent
Palmaz et al.

(10) Patent No.: US 6,190,404 B1
(45) Date of Patent: Feb. 20, 2001

(54) INTRAVASCULAR STENT AND METHOD FOR MANUFACTURING AN INTRAVASCULAR STENT

(75) Inventors: Julio C. Palmaz; Eugene A. Sprague, both of San Antonio, TX (US)

(73) Assignee: Advanced Bio Prosthetic Surfaces, Ltd., San Antonio, TX (US)

( * ) Notice: Under 35 U.S.C. 154(b), the term of this patent shall be extended for 0 days.

(21) Appl. No.: 09/187,178

(22) Filed: Nov. 5, 1998

Related U.S. Application Data

(60) Provisional application No. 60/064,916, filed on Nov. 7, 1997.

(51) Int. Cl.$^7$ .......................................................... A61F 2/06
(52) U.S. Cl. ............................................. 623/1.15; 623/901
(58) Field of Search ................................. 623/1, 12, 66, 623/1.15, 1.2, 1.21, 1.22, 1.18, 901; 600/36

(56) References Cited

U.S. PATENT DOCUMENTS

| 4,869,714 | 9/1989 | Deininger et al. |
| 5,728,150 | 3/1998 | McDonald et al. |

FOREIGN PATENT DOCUMENTS

| 0701803A1 | 3/1996 | (EP) . |
| 0850604A2 | 7/1998 | (EP) . |
| WO 97/42910 | 11/1997 | (WO) . |

OTHER PUBLICATIONS

J.C. Palmaz, Balloon–Expandable Intravascular Stent; *AJR*, vol. 150, pp. 1263–1269, Jun. 1998.

J.C. Palmaz, Intravascular Stents; *Syllabus for 77th Scientific Assembly and Annual Meeting*; Radiological Society of North America, pp. 185–192, 1991.

C. Hehrlein Et Al., Influence of surface texture and charge on the biocompatibility of endovascular stents, *Coronary Artery Disease*, vol. 6, No. 7, pp. 581–586, Jul. 1995.

E.A. Sprague Et Al., Human Aortic Endothelial Cell Migration onto Stent Surfaces under Static and Flow Conditions, *Journal of Vascular and Interventional Radiology*, vol. 8, No. 1, pp. 83–92, Jan.–Feb. 1997.

C. Oakley Et Al., Sensitivity of Fibroblasts and Their Cytoskeletons to Substratum Topographies: Topographic Guidance and Topographic Compensation by Micromachined Grooves of Different Dimensions, *Experimental Cell Research*, vol. 234, pp. 413–424, 1997.

B. Chehroudi Et Al., Titanium–coated micromachined grooves of different dimensions affect epithelial and connective–tissue cells differently in vivo, *Journal of Biomedical Materials Research*, vol. 24, pp. 1203–1219, 1990.

B. Chehroudi Et Al., Effects of a grooved titanium–coated implant surface on epithelial cell behavior in vitro and in vivo, *Journal of Biomedical Materials Research*, vol. 23, pp. 1067–1085, 1989.

L. Chou Et Al., Substratum surface topography alters cell shape and regulates fibronectin mRNA level, mRNA stability, secretion and assembly in human fibroblasts, *Journal of Cell Science*, vol. 108, 1995, pp. 1563–1573.

(List continued on next page.)

*Primary Examiner*—V. Millin
*Assistant Examiner*—Choon P. Koh
(74) *Attorney, Agent, or Firm*—Bracewell & Patterson, L.L.P.; Ben D. Tobor

(57) ABSTRACT

The invention relates to an intravascular stent wherein the intravascular stent has its inner surface treated to promote the migration of endothelial cells onto the inner surface of the intravascular stent. Particularly, the inner surface of the intravascular stent includes at least one groove. Methods for manufacturing an intravascular stent are also disclosed.

54 Claims, 4 Drawing Sheets

OTHER PUBLICATIONS

A. Damji Et Al., Directed Confrontations between Fibroblasts and Epithelial Cells on Micromachined Grooved Substrata, *Experimental Cell Research*, vol. 228, 1996, pp. 114–124.

C. Oakley Et Al., Topographic Compensation: Guidance and Directed Locomotion of Fibroblasts on Grooved Micromachined Substrata in the Absence of Microtubules, *Cell Motility and the Cytoskeleton*, vol. 31, 1995, pp. 45–58.

B. Chehroudi Et Al., A light and electron microscopic study of the effects of surface topography on the behavior of cells attached to titanium–coated percutaneous implants, *Journal of Biomedical Materials Research*, vol. 25, 1991, pp. 387–405.

B. Chehroudi Et Al., Computer–assisted three–dimensional reconstruction of epithelial cells attached to percutaneous implants, *Journal of Biomedical Materials Research*, vol. 29, 1995, pp. 371–379.

C. Oakley Et Al., The sequence of alignment of microtubules, focal contacts and actin filaments in fibroblasts spreading on smooth and grooved titanium substrata, *Journal of Cell Science*, vol. 106, 1993, pp. 343–354.

L. Chou Et Al., Effects of titanium on transcriptional and post–transcriptional regulation of fibronectin in human fibroblasts, *Journal of Biomedical Materials Research*, vol. 31, No. 2, 1996, pp. 209–217.

D.M. Brunette Et Al., Grooved Titanium Surfaces Orient Growth and Migration of Cells from Human Gingival Explants, *J. Dent Res*, vol. 62, No. 10, Oct. 1983, pp. 1045–1048.

T.R.L. Gould Et Al., The attachment mechanism of epithelial cells to titanium in vitro, *Journal of Periodontal Research*, vol. 16, 1981, pp. 611–616.

D.M. Brunette, Fibroblasts on Micromachined Substrata Orient Hierarchically to Grooves of Different Dimensions, *Experimental Cell Research*, vol. 164, 1986, pp. 11–26.

D.M. Brunette, The Effects of Implant Surface Topography on the Behavior of Cells, *The International Journal of Oral Maxillofacial Implants*, vol. 3, No. 4, 1988, pp. 231–246.

Buddy D. Ratner, Society for Biomaterials 1992 Presidential Address; Journal of Biomedical Materials Research, vol. 27, 837–850 (1993).

Julio C. Palmaz, M.D., New Advances in Endovascular Technology; Texas Heart Institute Journal; vol. 24, No. 3, 1997.

Campbell Rogers, M.D. and Elazer R. Edelman, M.D., PhD; Endovascular Stent Design Dictates Experimental Restenosis and Thrombosis, Sep. 22, 1994; *Circulation*, vol. 91, No. 12, pp. 2995–3001; Jun. 15, 1995.

V.A. DePalma, R.E. Baier, and J.W. Ford, Cornell Aeronautical Laboratory of Cornell University, Buffalo, NY, and V.L. Gott and A. Furuse, Johns Hopkins University School of Medicine, Baltimore, MD; Investigation of Three–Surface Properties of Several Metals and Their Relation to Blood Compatibility, *J. Biomed. Mater. Res. Symposium*, No. 3, pp. 37–75; © 1972 by John Wiley & Sons, Inc.

E.T. den Braber, J.E. de Ruijter, H.T.J. Smits, L.A. Ginsel, A.F. von Recum, and J.A. Jansen; Effect of parallel surface microgrooves and surface energy on cell growth; *Journal of Biomedical Materials Research*, vol. 29, 511–318 (1995).

P. Clark, P. Connolly, A.S.G. Curtis, J.A.T. Dow and C.D.W. Wilkinson; Topographical control of cell behaviour; ©*The Company of Biologists Limited 1987*; Development 99, 439–448 (1987).

Takehisa Matsuda and Takashi Sugawara; Control of cell adhesion, migration, and orientation on photochemically microprocessed surfaces; *Journal of Biomedical Materials Research*, vol. 32, 165–473 (1996); ©1996 John Wiley & Sons, Inc.

B. Wojciak–Stothard, A.S.G. Curtis, W. Monaghan, M. McGrath, I. Sommer, and C.D.W. Wilkinson; Role of the Cytoskeleton in the Reaction of Fibroblasts to Multiple Grooved Substrata; *Cell Motility And The Cytoskeleton*, vol. 31, 147–158 (1995).

P. Clark, P. Connolly, A.S.G. Curtis, J.A.T. Dow and C.D.W. Wilkinson; Topographical control of cell behaviour: II. multiple grooved substrata; ©*The Company of Biologists Limited 1990*; Development 108, 635–644 (1990).

P. Clark, P. Connolly, A.S.G. Curtis, J.A.T. Dow and C.D.W. Wilkinson; Cell guidance by ultrafine topography in vitro; ©*The Company of Biologists Limited 1991*; Journal of Cell Science 99, 73–77 (1991).

J.A.T. Dow, P. Clark, P. Connolly, A.S.G. Curtis and C.D.W. Wilkinson; Novel Methods for the Guidance and Monitoring of Single Cells and Simple Networks in Culture; ©*The Company of Biologists Limited 1987*; Journal of Cell Science Supp. 8, 55–79 (1987).

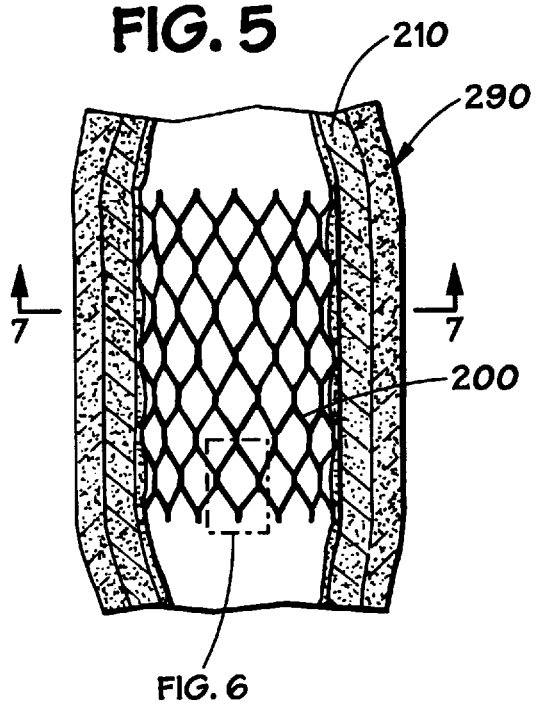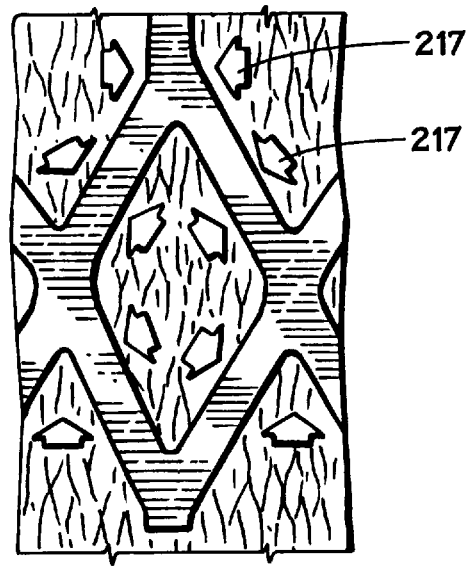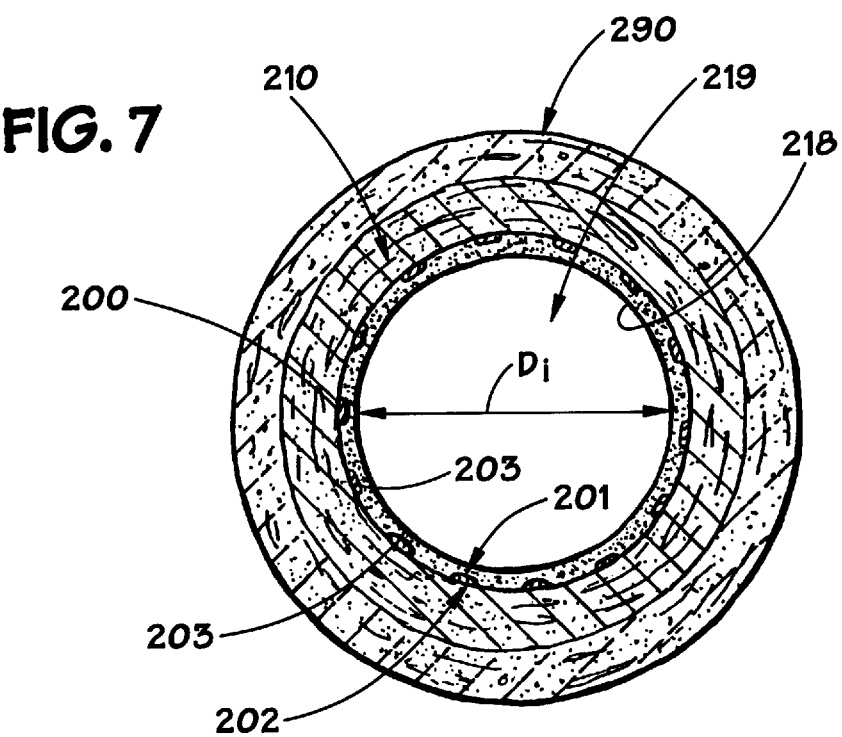

INTRAVASCULAR STENT AND METHOD FOR MANUFACTURING AN INTRAVASCULAR STENT

RELATED APPLICATIONS

This application claims the benefit of U.S. Provisional Application No. 60/064,916, filed Nov. 7, 1997.

BACKGROUND OF THE INVENTION

1. Field of the Invention

The invention relates to an intravascular stent and method for manufacturing an intravascular stent, wherein the intravascular stent has its inner surface treated to promote the migration of endothelial cells onto the inner surface of the intravascular stent.

2. Description of Related Art

Various types of intravascular stents have been used in recent years. An intravascular stent generally refers to a device used for the support of living tissue during the healing phase, including the support of internal structures. Intravascular stents, or stents, placed intraluminally, as by use of a catheter device, have been demonstrated to be highly efficacious in initially restoring patency to sites of vascular occlusion. Intravascular stents, or stents, may be of the balloon-expandable type, such as those of U.S. Pat. Nos. 4,733,665; 5,102,417; or 5,195,984, which are distributed by Johnson & Johnson Interventional Systems, of Warren, N.J., as the Palmaz™ and the Palmaz-Schatz™ balloon-expandable stents or balloon expandable stents of other manufacturers, as are known in the art. Other types of intravascular stents are known as self-expanding stents, such as Nitinol coil stents or self-expanding stents made of stainless steel wire formed into a zigzag tubular configuration.

Intravascular stents are used, in general, as a mechanical means to solve the most common problems of percutaneous balloon angioplasty, such as elastic recoil and intimal dissection. One problem intraluminal stent placement shares with other revascularization procedures, including bypass surgery and balloon angioplasty, is restenosis of the artery. An important factor contributing to this possible reocclusion at the site of stent placement is injury to, and loss of, the natural nonthrombogenic lining of the arterial lumen, the endothelium. Loss of the endothelium, exposing the thrombogenic arterial wall matrix proteins, along with the generally thrombogenic nature of prosthetic materials, initiates platelet deposition and activation of the coagulation cascade. Depending on a multitude of factors, such as activity of the fibrinolytic system, the use of anticoagulants, and the nature of the lesion substrate, the result of this process may range from a small mural to an occlusive thrombus. Secondly, loss of the endothelium at the interventional site may be critical to the development and extent of eventual intimal hyperplasia at the site. Previous studies have demonstrated that the presence of an intact endothelial layer at an injured arterial site can significantly inhibit the extent of smooth muscle cell-related intimal hyperplasia. Rapid reendothelialization of the arterial wall, as well as endothelialization of the prosthetic surface, or inner surface of the stent, are therefore critical for the prevention of low-flow thrombosis and for continued patency. Unless endothelial cells from another source are somehow introduced and seeded at the site, coverage of an injured area of endothelium is achieved primarily, at least initially, by migration of endothelial cells from adjacent arterial areas of intact endothelium.

Although an in vitro biological coating to a stent in the form of seeded endothelial cells on metal stents has been previously proposed, there are believed to be serious logistic problems related to live-cell seeding, which may prove to be insurmountable. Thus, it would be advantageous to increase the rate at which endothelial cells from adjacent arterial areas of intact endothelium migrate upon the inner surface of the stent exposed to the flow of blood through the artery. At present, most intravascular stents are manufactured of stainless steel and such stents become embedded in the arterial wall by tissue growth weeks to months after placement. This favorable outcome occurs consistently with any stent design, provided it has a reasonably low metal surface and does not obstruct the fluid, or blood, flow through the artery. Furthermore, because of the fluid dynamics along the inner arterial walls caused by blood pumping through the arteries, along with the blood/endothelium interface itself, it has been desired that the stents have a very smooth surface to facilitate migration of endothelial cells onto the surface of the stent. In fact, it has been reported that smoothness of the stent surface after expansion is crucial to the biocompatibility of a stent, and thus, any surface topography other than smooth is not desired. Christoph Hehriein, et. al., *Influence of Surface Texture and Charge On the Biocompatibility of Endovascular Stents, Coronary Artery Disease*, Vol. 6, pages 581–586 (1995). After the stent has been coated with serum proteins, the endothelium grows over the fibrin-coated metal surface on the inner surface of the stent until a continuous endothelial layer covers the stent surface, in days to weeks. Endothelium renders the thrombogenic metal surface protected from thrombus deposition, which is likely to form with slow or turbulent flow. At present, all intravascular stents made of stainless steel, or other alloys or metals, are provided with an extremely smooth surface finish, such as is usually obtained by electropolishing the metallic stent surfaces. Although presently known intravascular stents, specifically including the Palmaz™ and Palmaz-Schatz™ balloon-expandable stents have been demonstrated to be successful in the treatment of coronary disease, as an adjunct to balloon angioplasty, intravascular stents could be even more successful and efficacious, if the rate and/or speed of endothelial cell migration onto the inner surface of the stent could be increased. Accordingly, the art has sought an intravascular stent, and method for manufacturing an intravascular stent, which may increase the rate of migration of endothelial cells upon the inner surface of the stent after it has been implanted.

SUMMARY OF THE INVENTION

In accordance with the invention, the foregoing advantage has been achieved through the present intravascular stent having an outer surface and an inner surface. The present invention includes an improvement in such intravascular stents, and an improvement in the method for manufacturing such intravascular stents, by providing at least one groove disposed in the inner surface of the stent. A further feature of the present invention is that the at least one groove may have a width, a length, and a depth, and the width and depth may not vary along the length of the at least one groove. Further features of the present invention are that: the width of the groove may vary along the length of the at least one groove; the depth of the groove may vary along the length of the at least one groove; and both the width and the depth may vary along the length of the at least one groove.

Another feature of the present invention is that the at least one groove may have a length, a longitudinal axis, and a cross-sectional configuration, and the cross-sectional configuration of the at least one groove may vary along the length of the at least one groove. An additional feature of the present invention is that the cross-sectional configuration of the at least one groove may not vary along the length of the at least one groove. Further features of the present invention are that the cross-sectional configuration of the at least one groove may be: substantially symmetrical about the longitudinal axis of the at least one groove; substantially asymmetrical about the longitudinal axis of the at least one groove; substantially triangular shaped; substantially rectangular shaped; substantially square shaped; substantially U shaped; or substantially V shaped.

A further feature of the present invention is that the longitudinal axis of the at least one groove may be disposed: substantially parallel with the longitudinal axis of the stent; substantially perpendicular to the longitudinal axis of the stent; at an obtuse angle with respect to the longitudinal axis of the stent; or at an acute angle with respect to the longitudinal axis of the stent. An additional feature of the present invention is that the groove may have a depth within a range of approximately one-half to approximately ten microns, and the at least one groove may have a width within a range of approximately two to approximately forty microns.

It is believed that the improvements in intravascular stents and in methods for manufacturing intravascular stents of the present invention, when compared with presently known intravascular stents and methods for manufacturing such stents, has the advantage of increasing the rate of migration of endothelial cells upon the inner surface of the intravascular stent.

BRIEF DESCRIPTION OF THE DRAWING

In the drawing:

FIG. 5 is a partial cross-sectional view of the stent and artery of FIGS. 1 and 3 after a further passage of time;

FIG. 6 is an exploded view of the outlined portion of FIG. 5 denoted as FIG. 6;

FIG. 7 is a partial cross-sectional view of the stent and artery of FIG. 5, taken along lines 7—7 of FIG. 5, and illustrates rapid endothelialization resulting in a thin neointimal layer covering the stent;

While the invention will be described in connection with the preferred embodiment, it will be understood that it is not intended to limit the invention of that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1:
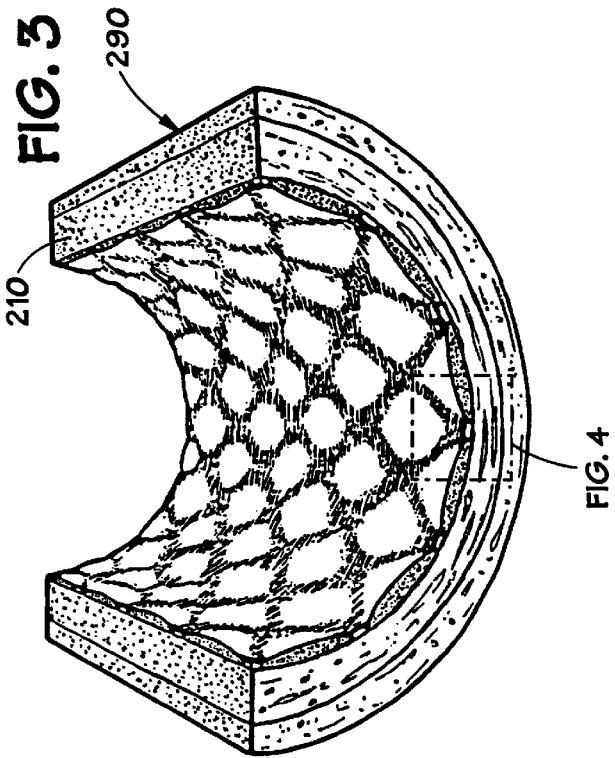
FIG. 1 is a partial cross-sectional, perspective view of a portion of a intravascular stent embedded within an arterial wall of a patient.
Figure 2:
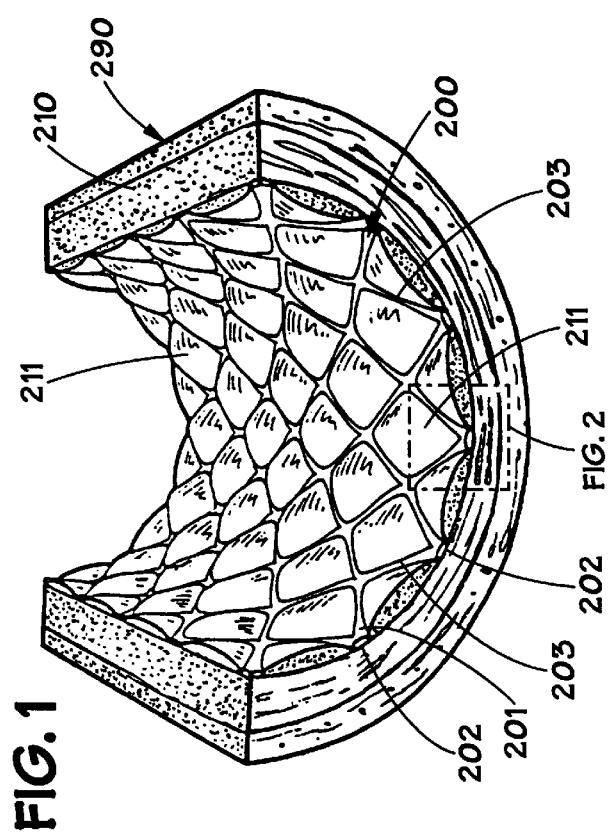
FIG. 2 is an exploded view of the outlined portion of FIG. 1 denoted as FIG. 2.

With reference to FIGS. 1 and 2, an intravascular stent 200 is illustrated being disposed within an artery 290 in engagement with arterial wall 210. For illustrative purposes only, intravascular stent 200, shown in FIGS. 1–6 is a Palmaz™ balloon-expandable stent, as is known in the art, stent 200 having an inner surface 201 and an outer surface 202. FIGS. 1 and 2 illustrate stent 200 shortly after it has been placed within artery 290, and after stent 200 has been embedded into arterial wall 210, as is known in the art. FIGS. 1 and 2 illustrate what may be generally characterized as correct placement of an intravascular stent. Stent 200 preferably includes a plurality of metal members, or struts, 203, which may be manufactured of stainless steel, or other metal materials, as is known in the art. As illustrated in FIGS. 1 and 2, correct placement of stent 200 results in tissue mounds 211 protruding between the struts 203, after struts 203 have been embedded in the arterial wall 210. Struts 203 also form troughs, or linear depressions, 204 in arterial wall 210. Dependent upon the degree of blockage of artery 290, and the type and amount of instrumentation utilized prior to placement of stent 200, the mounds of tissue 211 may retain endothelial cells (not shown).

Figure 3:
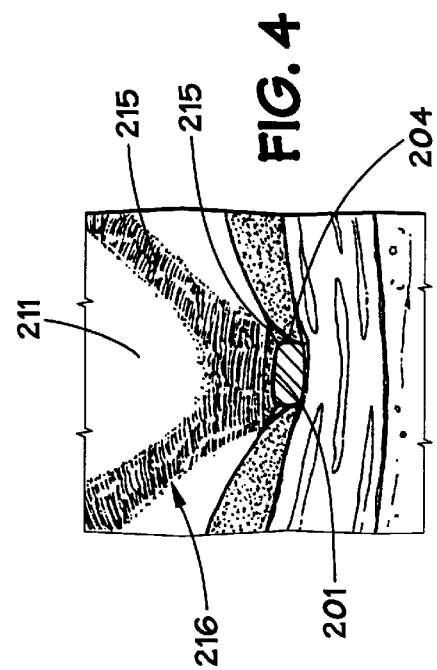
FIG. 3 is a partial cross-sectional, perspective view corresponding to FIG. 1 after the passage of time.
Figure 4:
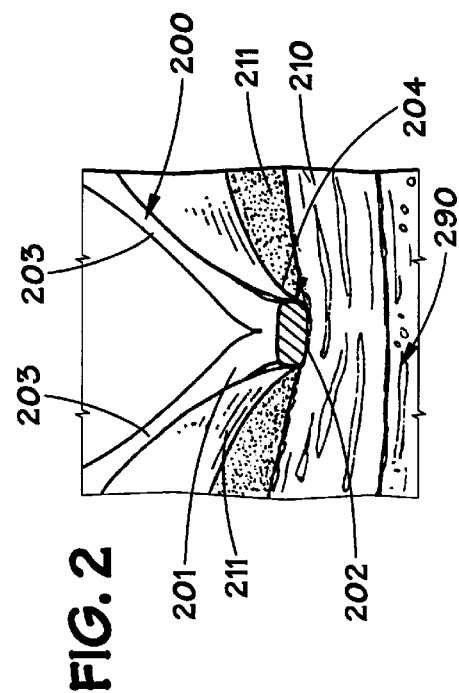
FIG. 4 is an exploded view of the outlined portion of FIG. 3 denoted as FIG. 4.

With reference to FIGS. 3 and 4, after the passage of time, a thin layer of thrombus 215 rapidly fills the depressions 204, and covers the inner surfaces 201 of stent 200. As seen in FIG. 4, the edges 216 of thrombus 215 feather toward the tissue mounds 211 protruding between the struts 203. The endothelial cells which were retained on tissue mounds 211 can provide for reendothelialization of arterial wall 210.

With reference to FIGS. 5 and 6, endothelial regeneration of artery wall 210 proceeds in a multicentric fashion, as illustrated by arrows 217, with the endothelial cells migrating to, and over, the struts 203 of stent 200 covered by thrombus 215. Assuming that the stent 200 has been properly implanted, or placed, as illustrated in FIGS. 1 and 2, the satisfactory, rapid endothelialization results in a thin tissue layer 218, as shown in FIG. 7. As is known in the art, to attain proper placement, or embedding, of stent 200, stent 200 must be slightly overexpanded. In the case of stent 200, which is a balloon-expandable stent, the balloon diameter chosen for the final expansion of stent 200 must be 10% to 15% larger than the matched diameter of the artery, or vessel, adjacent the site of implantation. As shown in FIG. 7, the diameter Di of the lumen 219 of artery 290 is satisfactory. If the reendothelialization of artery wall 210 is impaired by underexpansion of the stent or by excessive denudation of the arterial wall prior to, or during, stent placement, slower reendothelialization occurs. This results in increased thrombus deposition, proliferation of muscle cells, and a decreased luminal diameter Di, due to the formation of a thicker neointimal layer.

Figure 8:
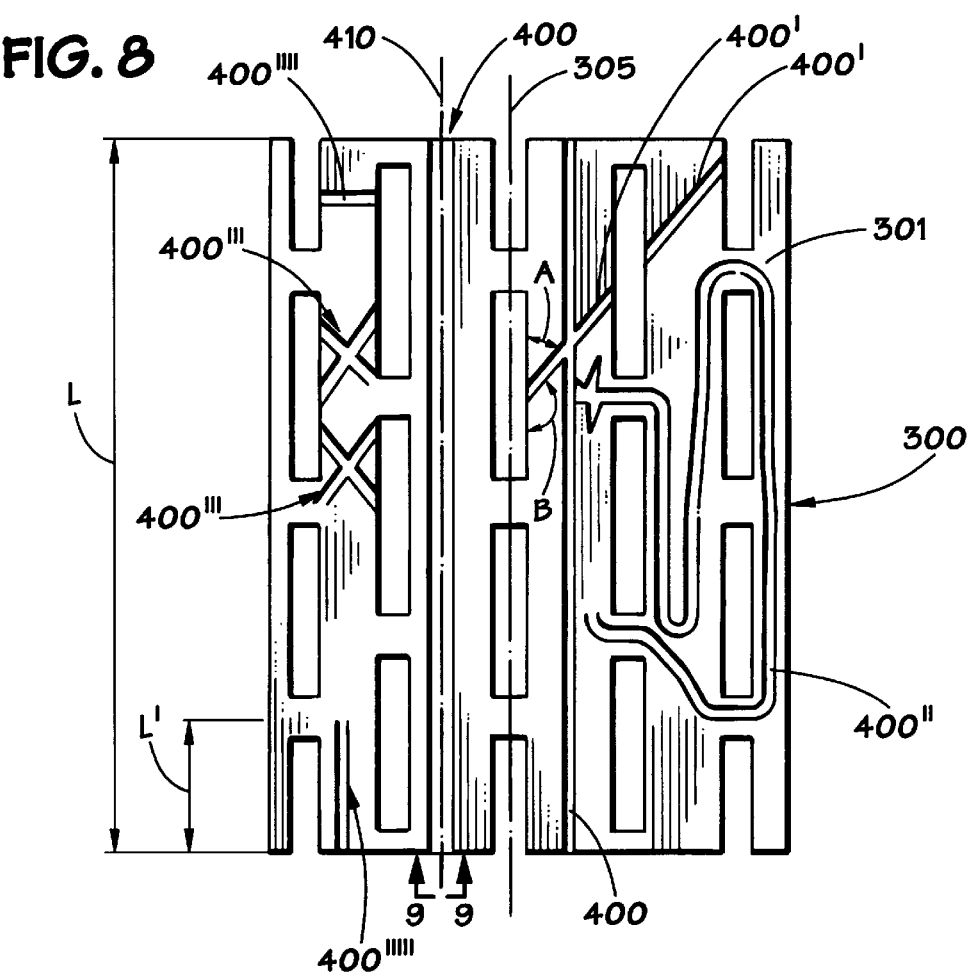
FIG. 8 is a plan view of an interior portion of an unexpanded intravascular stent in accordance with the present invention.

With reference to FIG. 8, an intravascular stent 300 in accordance with the present invention is illustrated. For illustrative purposes only, the structure of intravascular stent 300 is illustrated as being a Palmaz™ balloon-expandable stent, as is known in the art, illustrated in its initial, unexpanded configuration. It should be understood that the improvement of the present invention is believed to be suitable for use with any intravascular stent having any construction or made of any material as will be hereinafter described. Similarly, the improvement of the present invention in methods for manufacturing intravascular stents, is also believed to be applicable to the manufacturing of any type of intravascular stent as will also be hereinafter described.

As illustrated in FIG. 8, intravascular stent, or stent, 300 has an inner surface 301, and an outer surface 302, outer surface 302 normally being embedded into arterial wall 210 in an abutting relationship. In accordance with the present invention, the inner surface 301 of stent 300 is provided with at least one groove 400. If desired, as will be hereinafter described in greater detail, a plurality of grooves 400 could be provided on, or in, inner surface 301 of stent 300. The use of the term "groove" throughout this specification and in the claims is intended to be construed as: a channel or depression; a notch or a V-shaped or rounded indentation; or a scratch, or a mark, having been made with something sharp or jagged. The at least one groove 400, or grooves, of the present invention may be provided in, or on, the inner surface 301 of stent 300 in any suitable manner, such as by: abrading the inner surface 301 of stent 300 to provide the at least one groove 400; a chemical or mechanical etching process; use of a laser or laser etching process; use of a diamond-tipped tool; use of any suitable abrasive material; or use of any tool or process, which can provide the desired groove, or grooves, 400 in, or on, the inner surface 301 of stent 300, as will be hereinafter described in greater detail.

As shown in FIG. 8, the at least one groove, or grooves, 400 may be disposed with its longitudinal axis 410 being disposed substantially parallel with the longitudinal axis 305 of stent 300. Alternatively, the longitudinal axis 410 of the at least one groove 400 may be disposed substantially perpendicular to the longitudinal axis 305 of stent 300, as illustrated by groove 400''''; or the longitudinal axis 410 of the groove may be disposed at an obtuse, or acute, angle with respect to the longitudinal axis 305 of stent 300, as illustrated by groove 400'. The angle that groove 400' makes with respect to longitudinal axis 305 is either an acute or an obtuse angle dependent upon from which direction the angle is measured with respect to the longitudinal axis 305 of stent 300. For example, if the angle between the longitudinal axis of groove 400' and longitudinal axis 305 is measured as indicated by arrows A, the angle is an acute angle. If the angle is measured, as at arrows B, the angle is an obtuse angle.

Still with reference to FIG. 8, a plurality of grooves 400 may be provided on the inner surface 301 of stent 300, two grooves 400 being shown for illustrative purposes only. Instead of a plurality of individual grooves, such as grooves 400, a single groove 400'' could be provided in a serpentine fashion, so as to cover as much of the inner surface 301 of stent 300 as desired. Similarly, the grooves could be provided in a cross-hatched manner, or pattern, as shown by grooves 400'''. Grooves 400, 400', 400'', 400''', and 400'''' could be provided alone or in combination with each other, as desired, to provide whatever pattern of grooves is desired, including a symmetrical, or an asymmetrical, pattern of grooves. It should be noted that the angular disposition and location of the various grooves 400–400'''' will vary and be altered upon the expansion of stent 300 within artery 201 (FIG. 1), stent 300 being illustrated in its unexpanded configuration in FIG. 8. Similarly, if stent 300 were a stent made of wire or lengths of wire, the disposition and angular orientation of the grooves formed on such wire, or wire members, would similarly be altered upon the expansion and implantation of such stent. It should be further noted, as previously discussed, that the groove, or grooves, of the present invention may be provided in, or on, the inner surface of any intravascular stent, so as to increase the rate of migration of endothelial cells on, and over, the inner surface of the intravascular stent.

Figure 9:
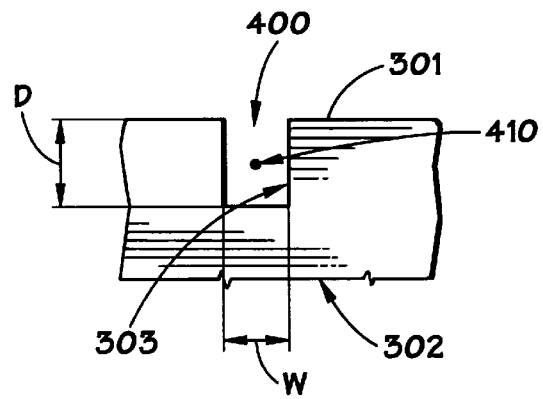
FIGS. 9–16 are various embodiments of an exploded view of a groove taken along line 9—9 of FIG. 8, illustrating various cross-sectional configurations and characteristics of various embodiments of grooves in accordance with the present invention.
Figure 10:
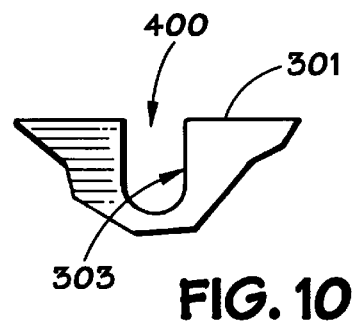
Figure 11:
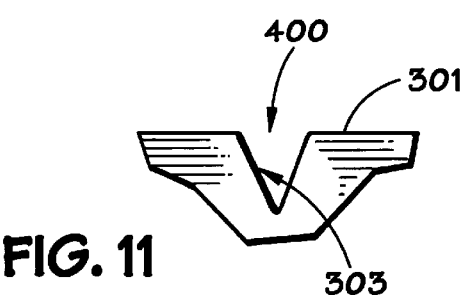
Figure 12:
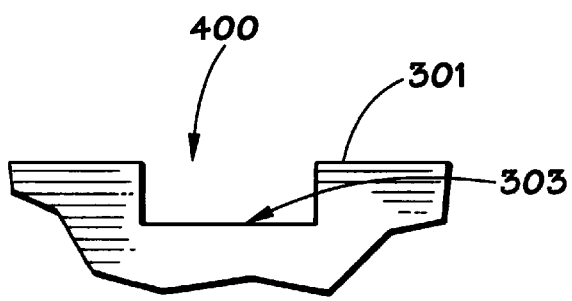

With reference to FIGS. 9–16, various embodiments of groove 400 will be described in greater detail. In general, as seen in FIG. 9, groove 400 has a width W, a depth D, and a length L (FIG. 8). The width W and depth D may be the same, and not vary, along the length L of the groove 400. Alternatively, the width W of the groove may vary along the length L of the groove 400. Alternatively, the depth D of the groove may vary along the length L of the at least one groove. Alternatively, both the width W and the depth D of the groove 400 may vary along the length of the at least one groove. Similarly, as with the location and angular disposition of groove, or grooves, 400 as described in connection with FIG. 8, the width W, depth D, and length L of the groove, or grooves, 400 can vary as desired, and different types and patterns of grooves 400 could be disposed on the inner surface 301 of stent 300.

Figure 13:
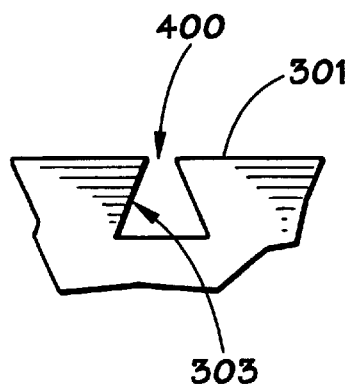
Figure 14:
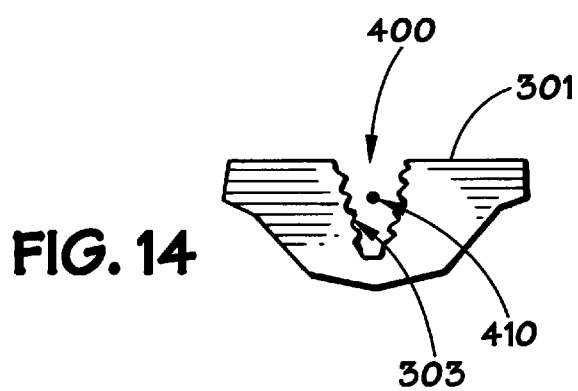
Figure 15:
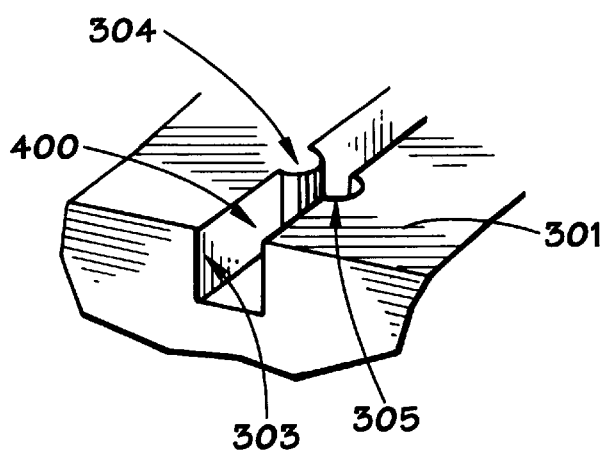
Figure 16:
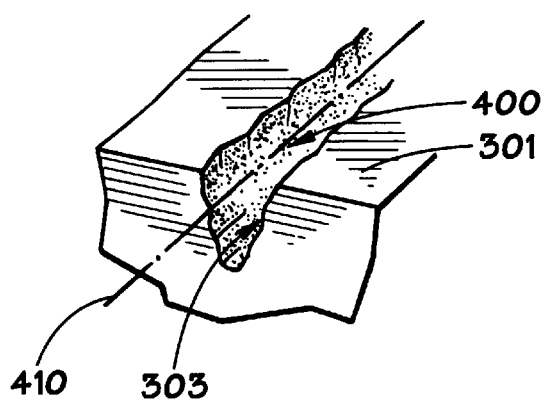

As shown in FIGS. 9–16, groove 400 may have a variety of different cross-sectional configurations. As desired, the cross-sectional configuration of the groove, or grooves, 400 may vary along the length L of the groove; or the cross-sectional configuration of the groove may not vary along the length of the at least one groove 400. Similarly, combinations of such cross-sectional configurations for the grooves could be utilized. The cross-sectional configuration of the groove, or grooves, 400 may be substantially symmetrical about the longitudinal axis 410 of groove 400 as illustrated in FIGS. 8 and 9; or the cross-sectional configuration of the at least one groove may be substantially asymmetrical about the longitudinal axis 410 of the least one groove, as illustrated in FIGS. 14 and 16. The cross-sectional configurations of groove 400 can assume a variety of shapes, some of which are illustrated in FIGS. 9–16, and include those cross-sectional configurations which are substantially: square shaped (FIG. 9); U shaped (FIG. 10); triangular, or V shaped (FIG. 11); rectangular shaped (FIG. 12); and triangular, or keyway shaped (FIG. 13). The wall surface 303 of each groove 400 may be substantially smooth, such as illustrated in FIGS. 9–13, or wall surface 303 may be jagged, or roughened, as illustrated in FIGS. 14 and 16. As illustrated in FIG. 15, wall surface 303 could also be provided with at least one protrusion 304 and at least one indentation 305 if desired, and additional protrusions and indentations 304, 305 could be provided as desired.

The depth D of groove, or grooves, 400 may fall within a range of approximately one-half to approximately ten microns. The width W of groove, or grooves, 400, may fall within a range of approximately two to approximately forty microns. Of course, the width W and depth D could be varied from the foregoing ranges, provided the rate of migration of endothelial cells onto stent 300 is not impaired. The length L of groove 400 may extend the entire length of stent 300, such as groove 400 of FIG. 8; or the length L' of a groove may be less than the entire length of stent 300, such as groove 400'''' in FIG. 8. The groove, or grooves, of the present invention may be continuous, or discontinuous, along inner surface 301 of stent 300.

The portion of the inner surface 301 of stent 300 which has not been provided with a groove, or grooves, 400 in accordance with the present invention, may have any suitable, or desired, surface finish, such as an electropolished surface, as is known in the art, or may be provided with whatever surface finish or coating is desired. It is believed that when at least one groove in accordance with the present invention is disposed, or provided, on, or in, the inner surface 301 of an intravascular stent 300, after the implantation of stent 300, the rate of migration of endothelial cells upon the inner surface 301 of stent 300 will be increased over that rate of migration which would be obtained if the inner surface 301 were not provided with at least one groove in accordance with the present invention.

It is to be understood that the invention is not limited to the exact details of construction, operation, exact materials, or embodiments shown and described, as obvious modifications and equivalents will be apparent to one skilled in the art. Accordingly, the invention is therefore to be limited only by the scope of the appended claims.

What is claimed is:

1. In a metallic intravascular stent having an outer surface and an inner surface, the improvement comprising:
at least one groove disposed in the inner surface of the stent, the at least one groove configured to have a shape adapted to increase the rate of endothelial cell migration upon the inner surface of the stent after the stent has been implanted.

2. The improvement of claim 1, wherein the at least one groove has a width, a length, and a depth.

3. The improvement of claim 2, wherein the width and depth do not vary along the length of the at least one groove.

4. The improvement of claim 2, wherein the width of the groove varies along the length of the at least one groove.

5. The improvement of claim 2, wherein the depth of the groove varies along the length of the at least one groove.

6. The improvement of claim 2, wherein the width and the depth vary along the length of the at least one groove.

7. The improvement of claim 1, wherein the at least one groove has a length, a longitudinal axis, and a cross-sectional configuration.

8. The improvement of claim 7, wherein the cross-sectional configuration of the at least one groove varies along the length of the at least one groove.

9. The improvement of claim 7, wherein the cross-sectional configuration of the at least one groove does not vary along the length of the at least one groove.

10. The improvement of claim 7, wherein the cross-sectional configuration of the at least one groove is substantially symmetrical about the longitudinal axis of the at least one groove.

11. The improvement of claim 7, wherein the cross-sectional configuration of the at least one groove is substantially asymmetrical about the longitudinal axis of the at least one groove.

12. The improvement of claim 7, wherein the cross-sectional configuration is substantially triangular shaped.

13. The improvement of claim 7, wherein the cross-sectional configuration is substantially rectangular shaped.

14. The improvement of claim 7, wherein the cross-sectional configuration is substantially square shaped.

15. The improvement of claim 7, wherein the cross-sectional configuration is substantially U shaped.

16. The improvement of claim 7, wherein the cross-sectional configuration is substantially V shaped.

17. The improvement of claim 1, wherein the stent and the at least one groove each have a longitudinal axis, and the longitudinal axis of the at least one groove is substantially parallel with the longitudinal axis of the stent.

18. The improvement of claim 1, wherein the stent and the at least one groove each have a longitudinal axis, and the longitudinal axis of the at least one groove is substantially perpendicular to the longitudinal axis of the stent.

19. The improvement of claim 1, wherein the stent and the at least one groove each have a longitudinal axis, and the longitudinal axis of the at least one groove is disposed at an obtuse angle with respect to the longitudinal axis of the stent.

20. The improvement of claim 1, wherein the stent and the at least one groove each have a longitudinal axis, and the longitudinal axis of the at least one groove is disposed at an acute angle with respect to the longitudinal axis of the stent.

21. The improvement of claim 1, wherein the at least one groove has a depth within a range of approximately one-half to approximately ten microns.

22. The improvement of claim 1, wherein the at least one groove has a width within a range of approximately two to approximately forty microns.

23. The improvement of claim 1, wherein at least two grooves are disposed in the inner surface of the stent and the at least two grooves are disposed in a cross-hatched pattern on the inner surface of the stent.

24. In a method for manufacturing a metallic intravascular stent, the stent having an outer surface and an inner surface, the improvement comprising:
providing at least one groove in the inner surface of the stent, the at least one groove configured to have a shape adapted to increase the rate of endothelial cell migration upon the inner surface of the stent after the stent has been implanted.

25. The improvement of claim 24, wherein the at least one groove has a width, a length, and a depth.

26. The improvement of claim 25, including the step of not varying the width and depth along the length of the at least one groove.

27. The improvement of claim 25, including the step of varying the width of the groove along the length of the at least one groove.

28. The improvement of claim 25, including the step of varying the depth of the groove along the length of the at least one groove.

29. The improvement of claim 25, including the step of varying the width and the depth along the length of the at least one groove.

30. The improvement of claim 24, wherein the at least one groove has a length, a longitudinal axis, and a cross-sectional configuration.

31. The improvement of claim 30, including the step of varying the cross-sectional configuration of the at least one groove along the length of the at least one groove.

32. The improvement of claim 30, including the step of varying the cross-sectional configuration of the at least one groove along the length of the at least one groove.

33. The improvement of claim 30, including the step of providing the cross-sectional configuration of the at least one groove substantially symmetrical about the longitudinal axis of the at least one groove.

34. The improvement of claim 30, including the step of providing the cross-sectional configuration of the at least one groove substantially asymmetrical about the longitudinal axis of the at least one groove.

35. The improvement of claim 30, including the step of providing the cross-sectional configuration as substantially triangular shaped.

36. The improvement of claim 30, including the step of providing the cross-sectional configuration as substantially rectangular shaped.

37. The improvement of claim 30, including the step of providing the cross-sectional configuration as substantially square shaped.

38. The improvement of claim 30, including the step of providing the cross-sectional configuration as substantially U shaped.

39. The improvement of claim 30, including the step of providing the cross-sectional configuration as substantially V shaped.

40. The improvement of claim 24, wherein the stent and the at least one groove each have a longitudinal axis, and including the step of providing the longitudinal axis of the at least one groove substantially parallel with the longitudinal axis of the stent.

41. The improvement of claim 24, wherein the stent and the at least one groove each have a longitudinal axis, and including the step of providing the longitudinal axis of the at least one groove substantially perpendicular to the longitudinal axis of the stent.

42. The improvement of claim 24, wherein the stent and the at least one groove each have a longitudinal axis, and including the step of providing the longitudinal axis of the at least one groove disposed at an obtuse angle with respect to the longitudinal axis of the stent.

43. The improvement of claim 24, wherein the stent and the at least one groove each have a longitudinal axis, and including the step of providing the longitudinal axis of the at least one groove disposed at an acute angle with respect to the longitudinal axis of the stent.

44. The improvement of claim 24, including the step of providing the at least one groove with a depth within a range of approximately one-half to approximately ten microns.

45. The improvement of claim 24, including the step of providing the at least one groove with a width within a range of approximately two to approximately forty microns.

46. The improvement of claim 24, including the step of providing at least two grooves in the inner surface of the stent and providing the at least two grooves in a cross-hatched pattern.

47. A method of manufacturing a metallic intravascular stent comprising the steps of:

forming an intravascular stent having an inner surface and an outer surface; and forming at least one groove on the inner surface of the intravascular stent, the at least one groove configured to have a shape adapted to increase the endothelial cell migration upon the inner surface of the stent after the stent has been implanted.

48. The method of claim 47, wherein the at least one groove is formed on the inner surface of the intravascular stent by abrading the inner surface.

49. The method of claim 47, wherein the at least one groove is formed on the inner surface of the intravascular stent by etching the inner surface with at least one chemical.

50. The method of claim 47, wherein the at least one groove is formed on the inner surface of the intravascular stent by etching the inner surface with a diamond tip tool.

51. The method of claim 47, wherein the at least one groove is formed on the inner surface of the intravascular stent by etching the inner surface with a mechanical tool.

52. The method of claim 47, wherein the at least one groove is formed on the inner surface of the intravascular stent by etching the inner surface with a laser.

53. The improvement of claim 1, wherein the stent has a longitudinal axis and at least a portion of the at least one groove is disposed substantially parallel to the longitudinal axis of the stent.

54. The improvement of claim 24, wherein the stent has a longitudinal axis, and including the step of disposing at least a portion of the at least one groove substantially parallel to the longitudinal axis of the stent.

* * * * *